(12) United States Patent
Greenberg et al.

(10) Patent No.: US 7,211,103 B2
(45) Date of Patent: May 1, 2007

(54) BIOCOMPATIBLE BONDING METHOD AND ELECTRONICS PACKAGE SUITABLE FOR IMPLANTATION

(75) Inventors: Robert J. Greenberg, Los Angeles, CA (US); Alfred E. Mann, Beverly Hills, CA (US); Neil Talbot, Montrose, CA (US); Jerry Ok, Canyon Country, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 696 days.

(21) Appl. No.: 10/174,349

(22) Filed: Jun. 17, 2002

(65) Prior Publication Data
US 2003/0233133 A1 Dec. 18, 2003

Related U.S. Application Data

(60) Provisional application No. 60/372,062, filed on Apr. 11, 2002.

(51) Int. Cl.
*A61N 1/00* (2006.01)
(52) U.S. Cl. .......................................... 607/1
(58) Field of Classification Search ............... 607/1–28
See application file for complete search history.

(56) References Cited

U.S. PATENT DOCUMENTS

| | | | |
|---|---|---|---|
| 3,699,970 A | 10/1972 | Brindley | |
| 4,573,481 A | 3/1986 | Bullara | |
| 4,837,049 A | 6/1989 | Byers | |
| 5,006,286 A * | 4/1991 | Dery et al. | 264/408 |
| 5,109,844 A | 5/1992 | de Juan | |
| 5,215,088 A | 6/1993 | Normann | |
| 5,468,936 A * | 11/1995 | Deevi et al. | 219/553 |
| 5,611,140 A | 3/1997 | Kulesza et al. | |
| 5,935,155 A | 8/1999 | Humayun | |
| 6,361,716 B1 * | 3/2002 | Kleyer et al. | 252/514 |

OTHER PUBLICATIONS

Hansjoerg Beutel, Thomas Stieglitz, Joerg Uwe Meyer, "Versatile 'Microflex'-Based Interconnection Technique," Proc. SPIE Conf on Smart Electronics and MEMS, San Diego, Cal., Mar. 1998, vol. 3328, pp. 174-182.
L. Del Castillo, R. Graber, S. D'Agostino, M. Mojarradi and A. Mottiwala, "Flip Chip Packaging of a MEMS Neuro-Prosthetic System," Proc. IMAPS International Conference & Exhibition on Advanced Packaging and Systems, Reno, Nevada, Mar. 2002, pp. 158-163.
M. Pourbaix, Atlas of Electrochemical Equilibria in Aqueous Solutions, National Assocation of Corrosion Engineers, Houston, 1974, pp. 399-405.

(Continued)

Primary Examiner—Scott M. Getzow
(74) Attorney, Agent, or Firm—Scott B. Dunbar; Tomas Lendvai; Gary Schnittgrund

(57) ABSTRACT

The invention is directed to a method of bonding a hermetically sealed electronics package to an electrode or a flexible circuit and the resulting electronics package, that is suitable for implantation in living tissue, such as for a retinal or cortical electrode array to enable restoration of sight to certain non-sighted individuals. The hermetically sealed electronics package is directly bonded to the flex circuit or electrode by one of several methods, including attachment by an electrically conductive adhesive, such as epoxy or polyimide, containing platinum metal flake in biocompatible glue; diffusion bonding of platinum bumps covered by an insulating layer; thermal welding of wire staples; or an integrated interconnect fabrication. The resulting electronic device is biocompatible and is suitable for long-term implantation in living tissue.

55 Claims, 9 Drawing Sheets

OTHER PUBLICATIONS

Joseph V. Mantese and William V. Alcini, "Platinum Wire Wedge Bonding: A New IC and Microsensor Interconnect," J. Electornic Materials, 17 (4) 1988, pp. 285-289.

Andreas Schneider, Thomas Stieglitz, Werner Haberer, Hansjorg Beutel, and J-Uwe Meyer, Flexible Interconnects for Biomedical Microsystems Assembly, IMAPS Conference, Jan. 31, 2002.

* cited by examiner

BIOCOMPATIBLE BONDING METHOD AND ELECTRONICS PACKAGE SUITABLE FOR IMPLANTATION

This application claims the benefit of U.S. Provisional Application No. 60/372,062, filed on Apr. 11, 2002, entitled "Platinum Deposition for Electrodes," the disclosure of which is incorporated herein by reference.

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to an electrode array or flexible circuit, electronics package and a method of bonding a flexible circuit or electrode array to an integrated circuit or electronics package.

BACKGROUND OF THE INVENTION

Arrays of electrodes for neural stimulation are commonly used for a variety of purposes. Some examples include U.S. Pat. No. 3,699,970 to Brindley, which describes an array of cortical electrodes for visual stimulation. Each electrode is attached to a separate inductive coil for signal and power. U.S. Pat. No. 4,573,481 to Bullara describes a helical electrode to be wrapped around an individual nerve fiber. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. U.S. Pat. No. 5,109,844 to de Juan describes a flat electrode array placed against the retina for visual stimulation. U.S. Pat. 5,935,155 to Humayun describes a retinal prosthesis for use with a flat retinal array.

Packaging of a biomedical device intended for implantation in the eye, and more specifically for physical contact with the retina, presents a unique interconnection challenge. The consistency of the retina is comparable to that of wet tissue paper and the biological media inside the eye is a corrosive saline liquid environment.

Thus, the device to be placed against the retina, in addition to being comprised of biocompatible, electrochemically stable materials, must appropriately conform to the curvature of the eye, being sufficiently flexible and gentle in contact with the retina to avoid tissue damage, as discussed by Andreas Schneider, Thomas Stieglitz, Werner Haberer, Hansjorg Beutel, and J.-Uwe Meyer, "Flexible Interconnects for Biomedical Microsystems Assembly, IMAPS Conference, Jan. 31, 2001. It is also desirable that this device, an electrode array, provides a maximum density of stimulation electrodes. A commonly accepted design for an electrode array is a very thin, flexible conductor cable. It is possible to fabricate a suitable electrode array using discrete wires, but with this approach, a high number of stimulation electrodes cannot be achieved without sacrificing cable flexibility (to a maximum of about 16 electrodes).

A lithographically fabricated thin film flex circuit electrode array overcomes such limitations. A thin film flex circuit electrode array can be made as thin as 10 μm (0.0004 inches) while accommodating about 60 electrodes in a single circuit routing layer. The flex circuit electrode array is essentially a passive conductor ribbon that is an array of electrode pads, on one end, that contact the retina and on the other end an array of bond pads that must individually mate electrically and mechanically to the electrical contacts of a hermetically sealed electronics package. These contacts may emerge on the outside of the hermetic package as an array of protruding pins or as vias flush to a package surface. A suitable interconnection method must not only serve as the interface between the two components, but must also provide electrical insulation between neighboring pathways and mechanical fastening between the two components.

Many methods exist in the electronics industry for attaching an integrated circuit to a flexible circuit. Commonly used methods include wire-bonding, anisotropic-conductive films, and "flip-chip" bumping. However, none of these methods results in a biocompatible connection. Common materials used in these connections are tin-lead solder, indium and gold. Each of these materials has limitations on its use as an implant. Lead is a known neurotoxin. Indium corrodes when placed in a saline environment. Gold, although relatively inert and biocompatible, migrates in a saline solution, when electric current is passed through it, resulting in unreliable connections.

In many implantable devices, the package contacts are feedthrough pins to which discrete wires are welded and subsequently encapsulated with polymer materials. Such is the case in heart pacemaker and cochlear implant devices. Flexible circuits are not commonly used, if at all, as external components of proven implant designs. The inventor is unaware of prior art describing the welding of contacts to flex circuits.

Attachment by gold ball bumping has been demonstrated by the Fraunhofer group (see Hansjoerg Beutel, Thomas Stieglitz,Joerg Uwe Meyer, "Versatile 'Microflex'-Based Interconnection Technique," Proc. SPIE Conf on Smart Electronics and MEMS, San Diego, Calif., March 1998, vol 3328, pp 174–82) to rivet a flex circuit onto an integrated circuit. A robust bond can be achieved in this way. However, encapsulation proves difficult to effectively implement with this method. Because the gap between the chip and the flex circuit is not uniform, underfill with epoxy is not practical. Thus, electrical insulation cannot be achieved with conventional underfill technology. Further, as briefly discussed earlier, gold, while biocompatible, is not completely stable under the conditions present in an implant device since it "dissolves" by electromigration when implanted in living tissue and subject to an electric current (see M. Pourbaix, Atlas of Electrochemical Equilibria in Aqueous Solutions, National Association of Corrosion Engineers, Houston, 1974, pp 399–405).

Widespread use of flexible circuits can be found in high volume consumer electronics and automotive applications, such as stereos. These applications are not constrained by a biological environment. Component assembly onto flex circuits is commonly achieved by solder attachment. These flex circuits are also much more robust and bulkier than a typical implantable device. The standard flex circuit on the market is no less than 0.002 inches in total thickness. The trace metalization is etched copper foil, rather than thin film metal. Chip-scale package (CSP) assembly onto these flex circuits is done in ball-grid array (BGA) format, which uses solder balls attached to input-output contacts on the package base as the interconnect structures. The CSP is aligned to a corresponding metal pad array on the flex circuit and subjected to a solder reflow to create the interconnection. A metallurgical interconnect is achieved by solder wetting. The CSP assembly is then underfilled with an epoxy material to insulate the solder bumps and to provide a pre-load force from the shrinkage of the epoxy.

Direct chip attach methods are referred to as chip-on-flex (COF) and chip-on-board (COB). There have been some assemblies that utilize gold wirebonding to interconnect bare, integrated circuits to flexible circuits. The flipchip process is becoming a reliable interconnect method. Flipchip technology originates from IBM's Controlled Collapse Chip Connection (C4) process, which evolved to solder reflow technique. Flipchip enables minimization of the package footprint, saving valuable space on the circuit, since it does not require a fan out of wirebonds. While there are a variety of flipchip configurations available, solder ball attach is the most common method of forming an interconnect. A less developed approach to flipchip bonding is the use of conductive adhesive, such as epoxy or polyimide, bumps to replace solder balls. These bumps are typically silver-filled epoxy or polyimide, although electrically conductive particulate of select biocompatible metal, such as platinum, iridium, titanium, platinum alloys, iridium alloys, or titanium alloys in dust, flake, or powder form, may alternatively be used. This method does not achieve a metallurgical bond, but relies on adhesion. Polymer bump flip chip also requires underfill encapsulation. Conceivably, polymer bump attachment could be used on a chip scale package as well. COB flipchip attach can also be achieved by using gold stud bumps, as an alternative to solder balls. The gold bumps of the chip are bonded to gold contacts on the hard substrate by heat and pressure. A recent development in chip-to-package attachment was introduced by Intel Corporation as Bumpless Build Up Layer (BBUL) technology. In this approach, the package is grown (built up) around the die rather than assembling the die into a pre-made package. BBUL presents numerous advantages in reliability and performance over flipchip.

Known techniques for bonding an electronic package to a flex circuit do not result in a hermetic package that is suitable for implantation in living tissue. Therefore, it is desired to have a method of attaching a rigid substrate to a flexible circuit that ensures that the bonded electronic package and flex circuit will function for long-term implant applications in living tissue.

SUMMARY OF THE INVENTION

An implantable electronic device comprising a hermetic electronics control unit, a first thin film flexible electrically insulating substrate; an electrically conducting metal layer deposited on the first insulating layer in electrical contact with the electronics control unit; a second thin film flexible electrically insulating substrate deposited on the electrically conducting metal layer; and a second flexible electrically insulating substrate defining holes that expose the electrically conducting metal layer.

A method of making an implantable electronic device comprising depositing a release coat on a hybrid substrate, depositing a first flexible electrically insulating substrate on the release coat; depositing an electrically conducting metal layer on the first flexible electrically insulating substrate, depositing a second flexible electrically insulating substrate on the metal layer, cutting said hybrid substrate to distinguish a carrier portion of said hybrid substrate, removing said release coat, removing at least a portion of said first flexible electrically insulating substrate from said carrier; creating voids in one of said flexible electrically insulating substrates to said metal layer creating a pattern of electrodes; bonding a microelectronics assembly to said hybrid substrate, and covering said microelectronics assembly with a hermetically sealed header.

The novel features of the invention are set forth with particularity in the appended claims. The invention will be best understood from the following description when read in conjunction with the accompanying drawings.

OBJECTS OF THE INVENTION

It is an object of the invention to provide a hermetic, biocompatible electronics package that is attached to a flexible circuit.

It is an object of the invention to attach a hermetically sealed electronics package to a flexible circuit for implantation in living tissue.

It is an object of the invention to attach a hermetically sealed electronics package to a flexible circuit for implantation in living tissue to transmit electrical signals to living tissue, such as the retina.

It is an object of the invention to provide a hermetic, biocompatible electronics package that is attached directly to a rigid substrate.

Other objects, advantages and novel features of the present invention will become apparent from the following detailed description of the invention when considered in conjunction with the accompanying drawing.

DETAILED DESCRIPTION OF THE PREFERRED EMBODIMENTS

The following description is the best mode presently contemplated for carrying out the invention. This description is not to be taken in a limiting sense, but is made merely for describing the general principles of the invention. The scope of the invention should be determined with reference to the claims.

Figure 1:
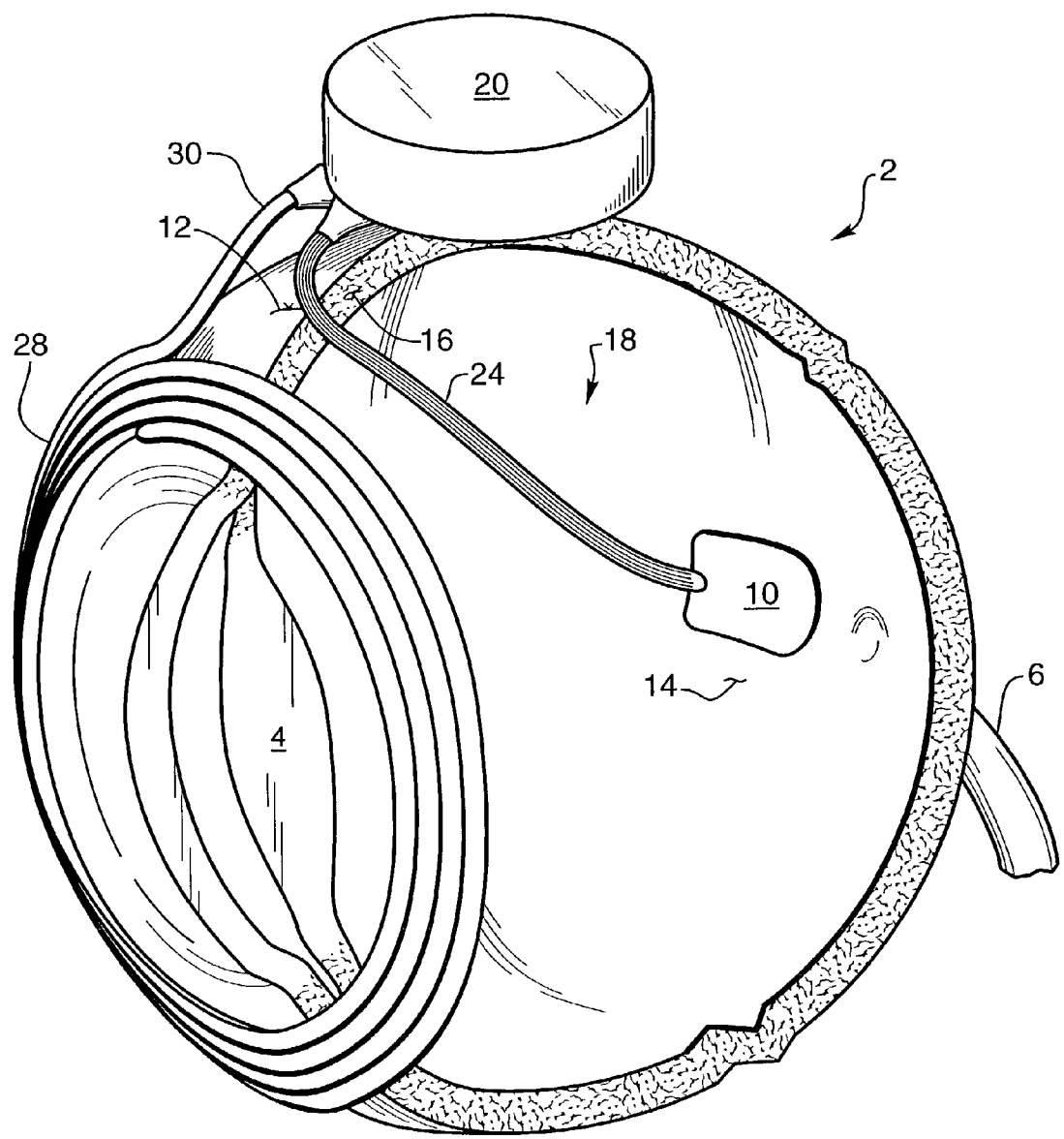
FIG. 1 illustrates a perspective cutaway view of an eye containing a flexible circuit electrode array.

The present invention provides a flexible circuit electronics package and a method of bonding a flexible circuit to a hermetic integrated circuit which is useful for a number of applications, including implantation in living tissue as a neural interface, such as a retinal electrode array or an electrical sensor. The tissue paper thin flexible circuit 18, FIG. 1, transmits electrical signals to the eye 2 by means of electrodes, that are located in a stimulating electrode array 10, that are in contact with the retina 14. It is obvious that in addition to a stimulating electrode array or sensing electrode, the electrodes may be contacts connecting to remote electrodes. FIG. 1 illustrates the electronics control unit 20 in a perspective cutaway view of an eye 2 containing a flexible circuit electrode array 18. The electronics control unit 20 is hermetically sealed. The electronics control unit 20 may be a hermetic ceramic case with electronics inside, or it may be a hermetically sealed integrated circuit, or any other environmentally sealed electronics package. The stimulating electrode array 10 is implanted on the retina 14. Flexible circuit ribbon 24 connects the stimulating electrode array 10 to the electronics control unit 20.

The flexible circuit ribbon 24 preferably passes through the sclera 16 of the eye 2 at incision 12. Another embodiment of the invention is the flexible circuit ribbon 24 replaced by alternative means of electrical interconnection, such as fine wires or thin cable. The lens 4 of the eye 2 is located opposite the retina 14. A coil 28, which detects electronic signals such as of images or to charge the electronics control unit 20 power supply, located outside the eye 2, near the lens 4, is connected to the electronics control unit 20 by wire 30.

Figure 2:
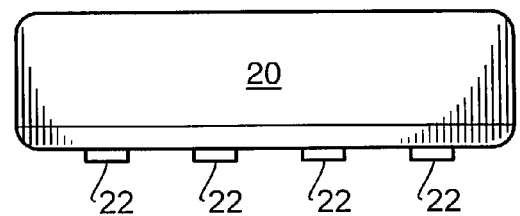
FIG. 2 is a side view of an electronics package.

FIG. 2 illustrates a side view of the hermetic electronics control unit 20 and the input/output contacts 22 that are located on the bottom of the unit 20. The input/output contacts 22 are bonded in the completed assembly to the flexible circuit 18. Thick film pad 23 is formed by known thick film technology, such as silk screening or plating.

Figure 3:
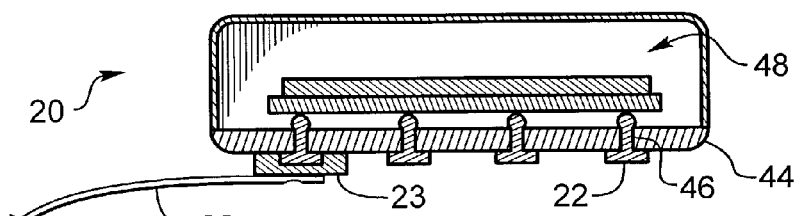
FIG. 3 illustrates a cutaway side view of an electronics package.

FIG. 3 illustrates a cutaway side view of the hermetic electronics control unit 20. The pad 23 facilitates attachment of wire 30, and is preferably comprised of a biocompatible material such as platinum, iridium, or alloys thereof, and is preferably comprised of platinum. Wire 30 is preferably bonded to pad 23 by welding (see FIG. 3). The microelectronics assembly 48 is mounted on the hybrid substrate 44. Vias 46 pass through the substrate 44 to input/output contacts 22. Electrical signals arrive by wire 30 and exit the electronics control unit 20 by input/output contacts 22.

Figure 4:
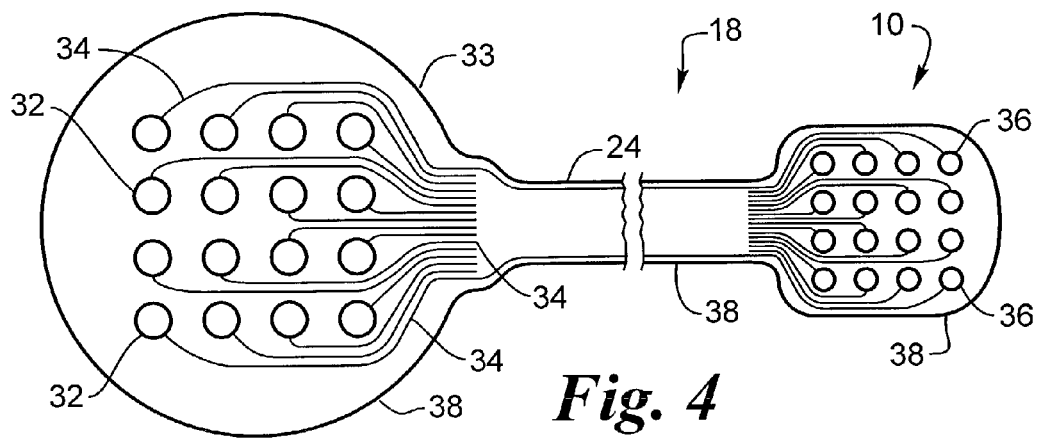
FIG. 4 is a top view of a flex circuit without the electronics package.

A top view of the flexible circuit 18 is illustrated in FIG. 4. Electrical signals from the electronics control unit 20 (see FIG. 3) pass into bond pads 32, which are mounted in bond pad end 33. Flexible electrically insulating substrate 38, is preferably comprised of polyimide. The signals pass from the bond pads 32 along traces 34, which pass along flexible circuit ribbon 24 to the stimulating electrode array 10. The array 10 contains the electrodes 36, which are implanted to make electrical contact with the retina 14 of the eye 2, illustrated in FIG. 1. An alternative bed of nails embodiment for the electrodes 36 is disclosed by Byers, et al. in U.S. Pat. No. 4,837,049.

Figure 5:
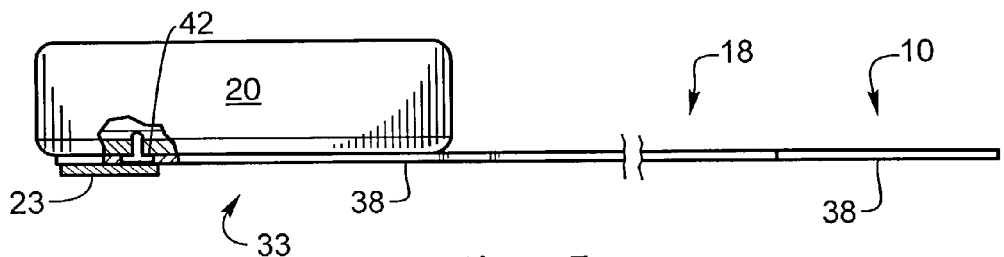
FIG. 5 presents a side view of a flex circuit with the electronics package.

In FIG. 5, the hermetic electronics control unit 20 is illustrated mounted to flexible circuit 18. In order to assure electrical continuity between the electronics control unit 20 and the flexible circuit 18, the electrical control unit 20 must be intimately bonded to the flexible circuit 18 on the bond pad end 33. A cutaway of the electronics control unit 20 (FIG. 5) illustrates a bonded connection 42. The flexible electrically insulating substrate 38 is very thin and flexible and is able to conform to the curvature of the retina 14 (FIG. 1), when implanted thereon.

Methods of bonding the flexible insulating substrate 18 to the hermetic electronics control unit 20 are discussed next.

Platinum Conductor in Polymer Adhesive

Figure 6:
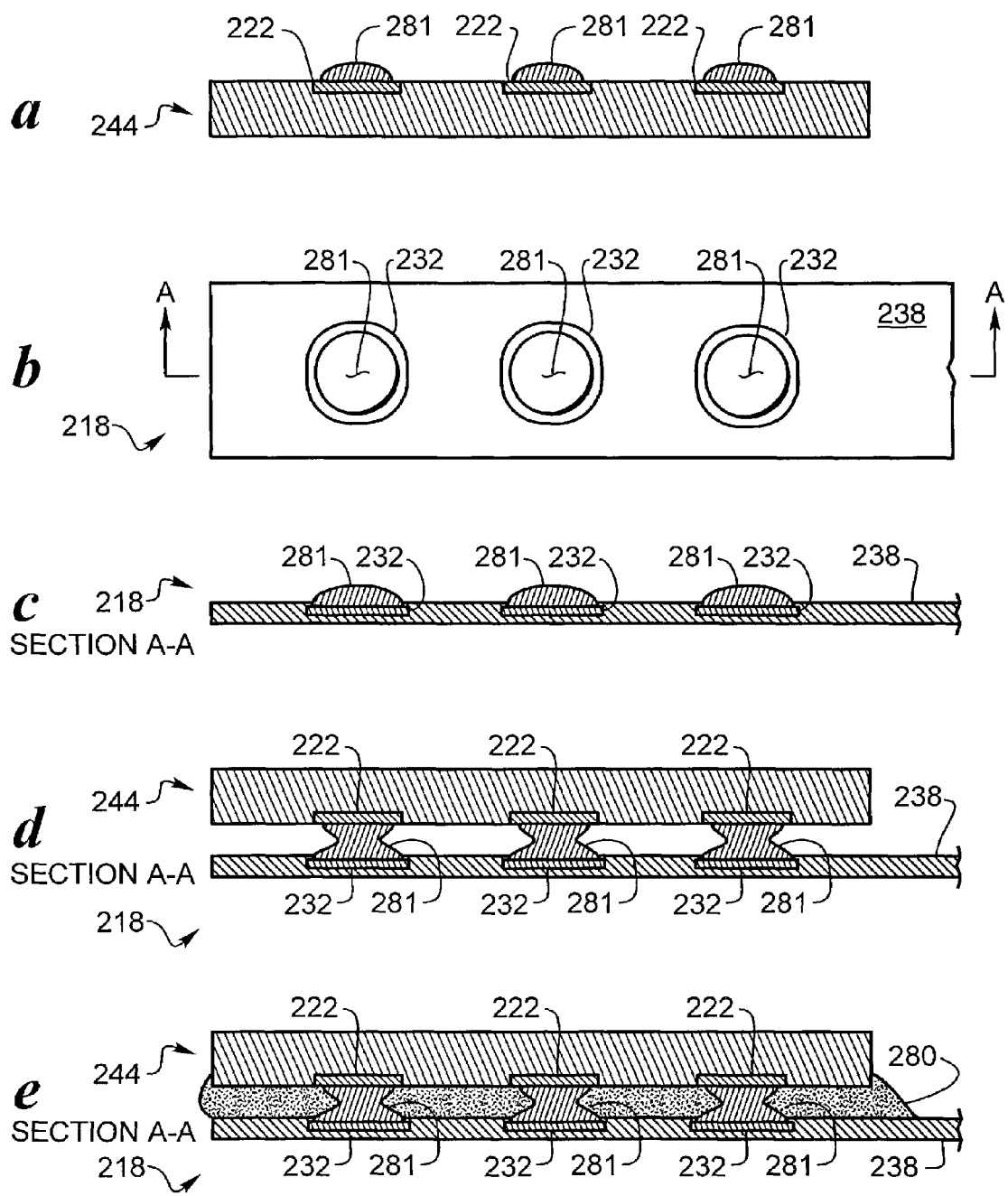
FIG. 6 is a side view of a flex circuit that is bonded with adhesive to a hybrid substrate.

A preferred embodiment of the invention, illustrated in FIG. 6, shows the method of bonding the hybrid substrate 244 to the flexible circuit 218 using electrically conductive adhesive 281, such as a polymer, which may include polystyrene, epoxy, or polyimide, which contains electrically conductive particulate of select biocompatible metal, such as platinum, iridium, titanium, platinum alloys, iridium alloys, or titanium alloys in dust, flake, or powder form.

In FIG. 6, step a, the hybrid substrate 244, which may alternatively be an integrated circuit or electronic array, and the input/output contacts 222 are prepared for bonding by placing conductive adhesive 281 on the input/output contacts 222. The rigid integrated circuit 244 is preferably comprised of a ceramic, such as alumina or silicon. In step b, the flexible circuit 218 is preferably prepared for bonding to the hybrid substrate 244 by placing conductive adhesive 281 on bond pads 232. Alternatively, the adhesive 281 may be coated with an electrically conductive biocompatible metal. The flexible circuit 218 contains the flexible electrically insulating substrate 238, which is preferably comprised of polyimide. The bond pads 232 are preferably comprised of an electrically conductive material that is biocompatible when implanted in living tissue, and are preferably platinum or a platinum alloy, such as platinum-iridium.

FIG. 6, step c illustrates the cross-sectional view A—A of step b. The conductive adhesive 281 is shown in contact with and resting on the bond pads 232. Step d shows the hybrid substrate 244 in position to be bonded to the flexible circuit 218. The conductive adhesive 281 provides an electrical path between the input/output contacts 222 and the bond pads 232. Step e illustrates the completed bonded assembly wherein the flexible circuit 218 is bonded to the hybrid substrate 144, thereby providing a path for electrical signals to pass to the living tissue from the electronics control unit (not illustrated). The assembly has been electrically isolated and hermetically sealed with adhesive underfill 280, which is preferably epoxy.

Studbump Bonding

Figure 7:
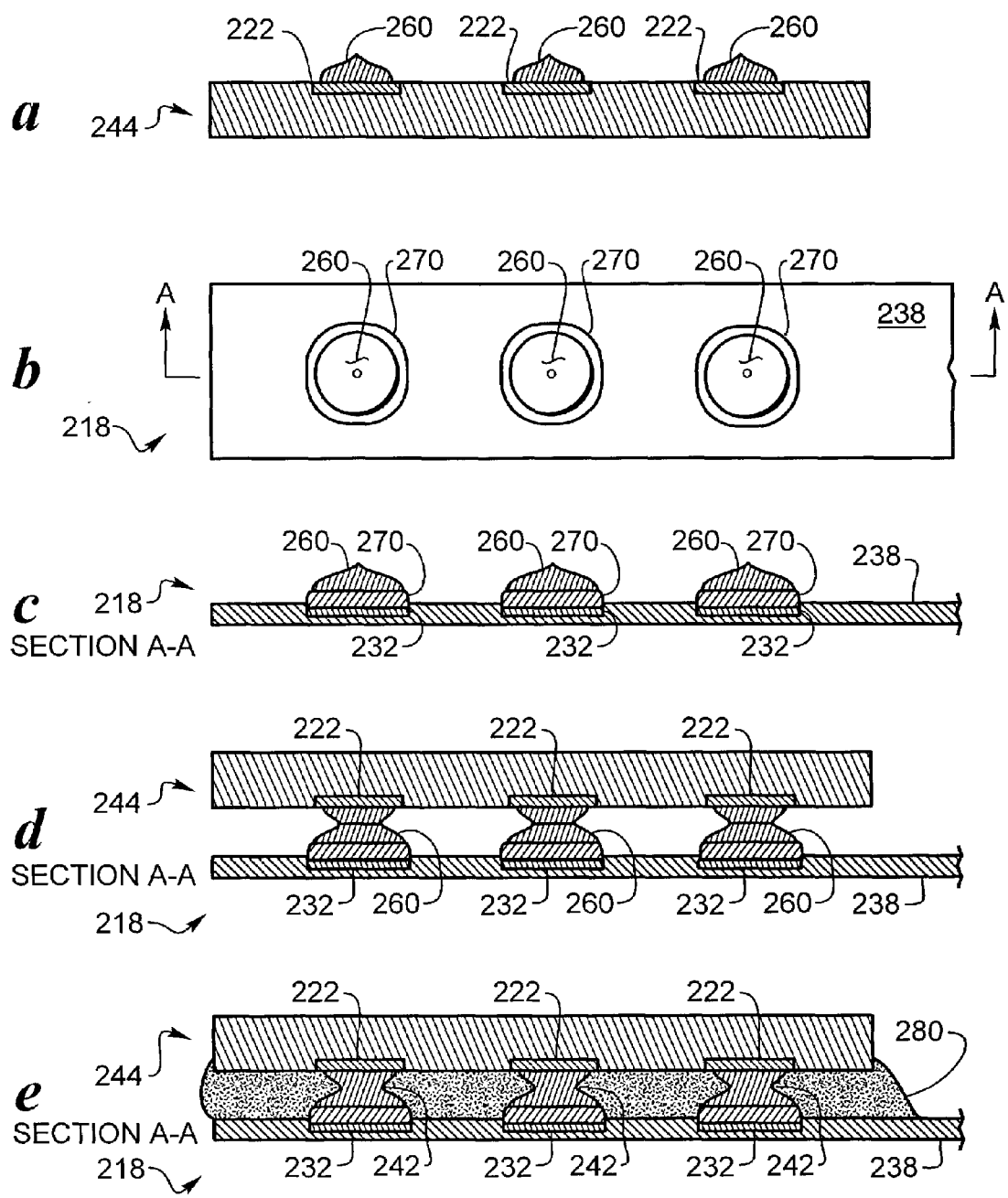
FIG. 7 is a series of illustrations of a flexible circuit being bonded using conductive metal pads to a hybrid substrate.

FIG. 7 illustrates the steps of an alternative embodiment to bond the hybrid substrate 244 to flexible circuit 218 by studbumping the hybrid substrate 244 and flexible electrically insulating substrate 238 prior to bonding the two components together by a combination of heat and/or pressure, such as ultrasonic energy. In step a, the hybrid substrate 244 is prepared for bonding by forming a studbump 260 on the input/output contacts 222. The studbump is formed by known methods and is preferably comprised of an electrically conductive material that is biocompatible when implanted in living tissue if exposed to a saline environment. It is preferably comprised of metal, preferably biocompatible metal, or gold or of gold alloys. If gold is selected, then it must be protected with a water resistant adhesive or underfill 280.

Alternatively, the studbump 260 may be comprised of an insulating material, such as an adhesive or a polymer, which is coated with an electrically conductive coating of a material that is biocompatible and stable when implanted in living tissue, while an electric current is passed through the studbump 260. One such material coating may preferably be platinum or alloys of platinum, such as platinum-iridium, where the coating may be deposited by vapor deposition, such as by ion-beam assisted deposition, or electrochemical means.

FIG. 7, step b presents the flexible circuit 218, which comprises the flexible electrically insulating substrate 238 and bond pads 232. The flexible circuit 218 is prepared for bonding by the plating bond pads 232 with an electrically conductive material that is biocompatible when implanted in living tissue, such as with a coating of platinum or a platinum alloy. Studbumps 260 are then formed on the plated pad 270 by known methods. Step c illustrates cross-section A—A of step b, wherein the flexible circuit 218 is ready to be mated with the hybrid substrate 244.

FIG. 7, step d illustrates the assembly of hybrid substrate 244 flipped and ready to be bonded to flexible circuit 218. Prior to bonding, the studbumps 260 on either side may be flattened by known techniques such as coining. Pressure is applied to urge the mated studbumps 260 together as heat is applied to cause the studbumps to bond by a diffusion or a melting process. The bond may preferably be achieved by thermosonic or thermocompression bonding, yielding a strong, electrically conductive bonded connection 242, as illustrated in step e. An example of a thermosonic bonding method is ultrasound. The bonded assembly is completed by placing an adhesive underfill 280 between the flexible circuit 218 and the hybrid substrate 244, also increasing the strength of the bonded assembly and electrically isolating each bonded connection. The adhesive underfill 280 is preferably epoxy.

Weld Staple Interconnect

Figure 8:
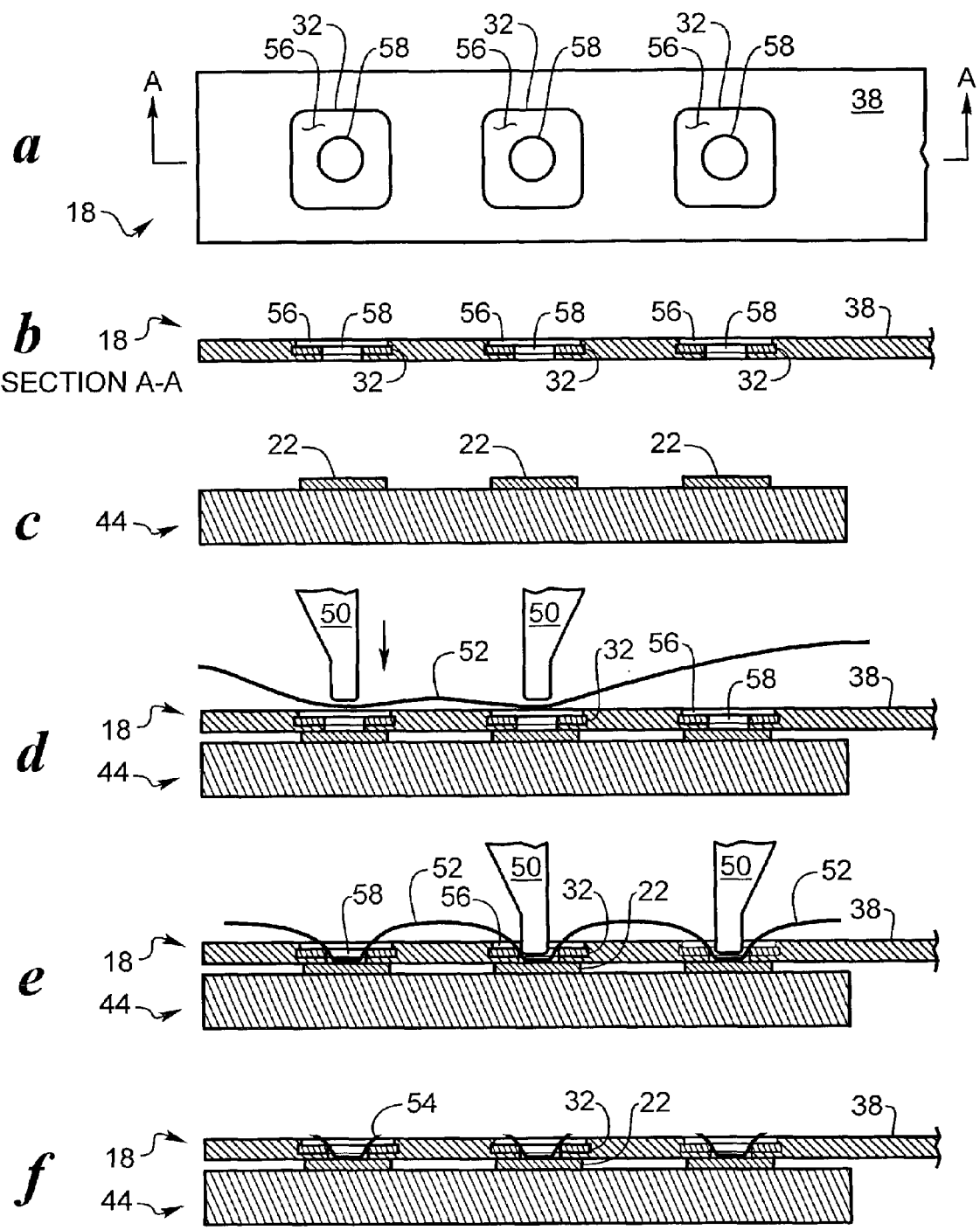
FIG. 8 is a series of illustrations of weld staple bonding of a flexible circuit to a hybrid substrate.

FIG. 8 illustrates the steps of a further alternative embodiment to bond the hybrid substrate 44 to flexible circuit 18 by weld staple bonding the substrate 244 and flexible electrically insulating substrate 38 together. In step a, a top view of the flexible circuit 18 is shown. Flexible circuit 18 is comprised of flexible electrically insulating substrate 38, which is preferably polyimide, and bond pads 32 having a through hole 58 therethrough each bond pad 32 and through the top and bottom surfaces of flexible circuit 18. The bond pads 32 are comprised of an electrically conductive and biocompatible material which is stable when implanted in living tissue, and which is preferably platinum or a platinum alloy, such as platinum-iridium.

FIG. 8, step b presents section A—A, which is shown in the illustration of step a. The through holes 58 pass completely through each bond pad 58, preferably in the center of the bond pad 58. They are preferably formed by plasma etching. The bond pads 58 are not covered on the top surface of flexible circuit 18 by flexible electrically insulating substrate 38, thereby creating bond pad voids 56.

FIG. 8, step c shows the side view of hybrid substrate 44 with input/output contacts 22 on one surface thereof. The hybrid substrate 44 is positioned, in step d, to be bonded to the flexible circuit 18 by placing the parts together such that the input/output contacts 22 are aligned with the bond pads 32. Then wire 52, which is preferably a wire, but may equally well be a ribbon or sheet of weldable material, that is also preferably electrically conductive and biocompatible when implanted in living tissue, is attached to input/output contact 22 and bond pad 32 to bond each aligned pair together. The wire 52 is preferably comprised of platinum, or alloys of platinum, such as platinum-iridium. The bond is preferably formed by welding using the parallel gap welder 50, which moves up and down to force the wire 52 into the through hole 58 and into contact with input/output contact 22. This process is repeated for each aligned set of input/output contacts 22 and bond pads 32, as shown in step e.

The weld staple interconnect bonding process is completed, as shown in step f, by cutting the wire 54, leaving each aligned set of input/output contacts 22 and bond pads 32 electrically connected and mechanically bonded together by staple 54.

Tail-Latch Interconnect

Figure 9:
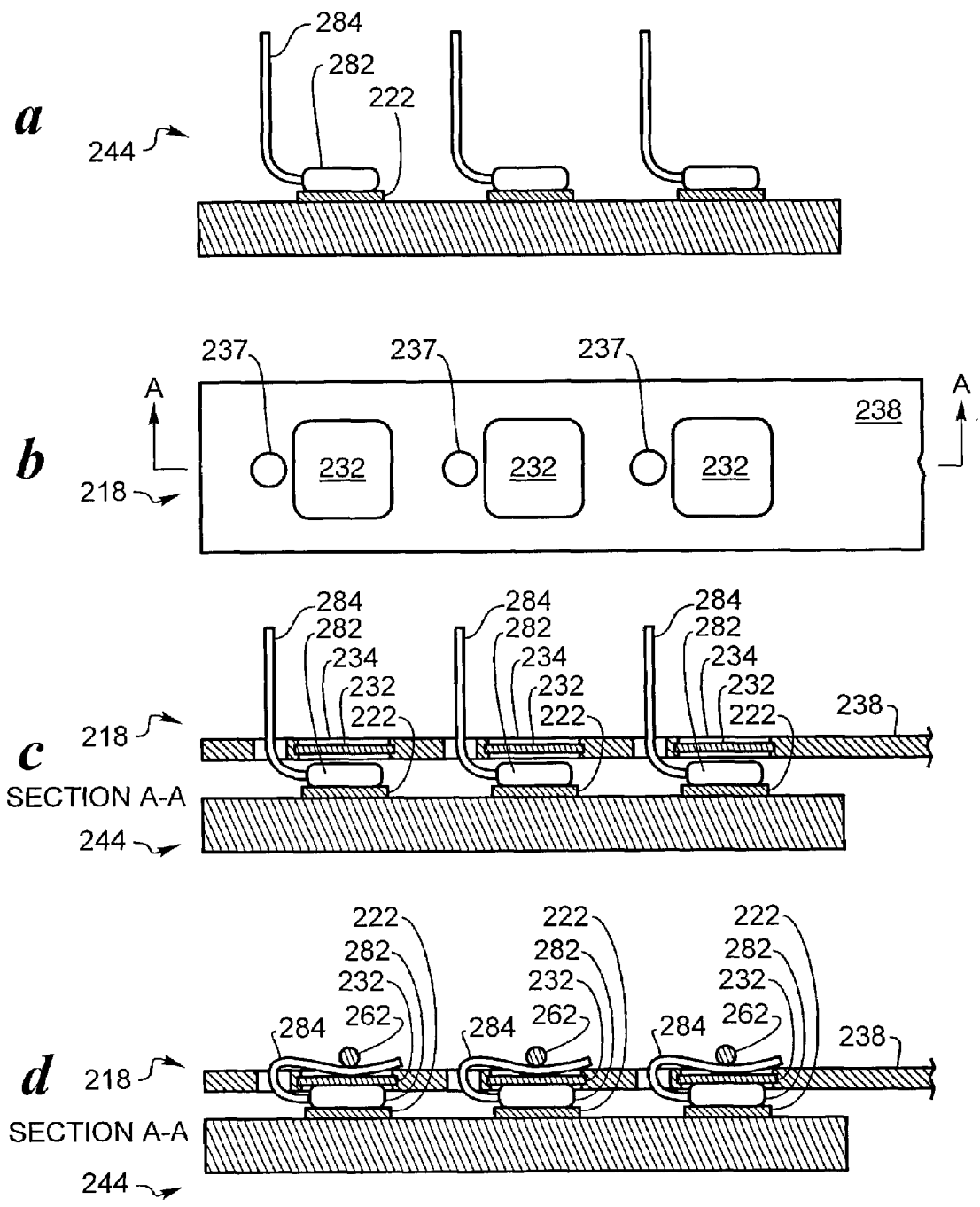
FIG. 9 is a sequence of steps illustrating tail-latch interconnect bonding of a flexible circuit to a hybrid substrate.

FIG. 9 illustrates yet another embodiment for attaching the hybrid substrate 244 to a flexible circuit 218 by using a tail-ball 282 component, as shown in step a. The hybrid substrate 244 is preferably comprised of a ceramic material, such as alumina or silicon. In one embodiment, a wire, preferably made of platinum or another electrically conductive, biocompatible material, is fabricated to have a ball on one end, like the preferred tail-ball 282 illustrated in step a. The tail-ball 282 has tail 284 attached thereto, as shown in the side view of step a. The tail-ball 282 is aligned with input/output contact 222 on hybrid substrate 244, in preparation to being bonded to flexible circuit 218, illustrated in step b.

The top view of step b illustrates flexible electrically insulating substrate 238, which is preferably comprised of polyimide, having the through hole 237 passing completely thorough the thickness and aligned with the tail 284. The bond pads 232 are exposed on both the top and bottom surfaces of the flexible circuit 218, by voids 234, enabling electrical contact to be made with input/output contacts 222 of the hybrid substrate 244. The voids are preferably formed by plasma etching.

The side view of FIG. 9, step c, which illustrates the section A—A of step b, shows the hybrid substrate 244 in position to be bonded to and aligned with flexible circuit 218. The tails 284 are each placed in through hole 237. Pressure is applied and the tail-balls 282 are placed in intimate contact with bond pads 232 and input/output contacts 222. Step c illustrates that each of the tails 284 is bent to make contact with the bond pads 232. The bonding process is completed by bonding, preferably by welding, each of the tails 284, bond pads 232, tail-balls 282, and input/output contacts 222 together, thus forming a mechanical and electrical bond. Locking wire 262 is an optional addition to assure that physical contact is achieved in the bonded component. The process is completed by underfilling the gap with an electrically insulating and biocompatible material (not illustrated), such as epoxy.

Integrated Interconnect by Vapor Deposition

Figure 10:
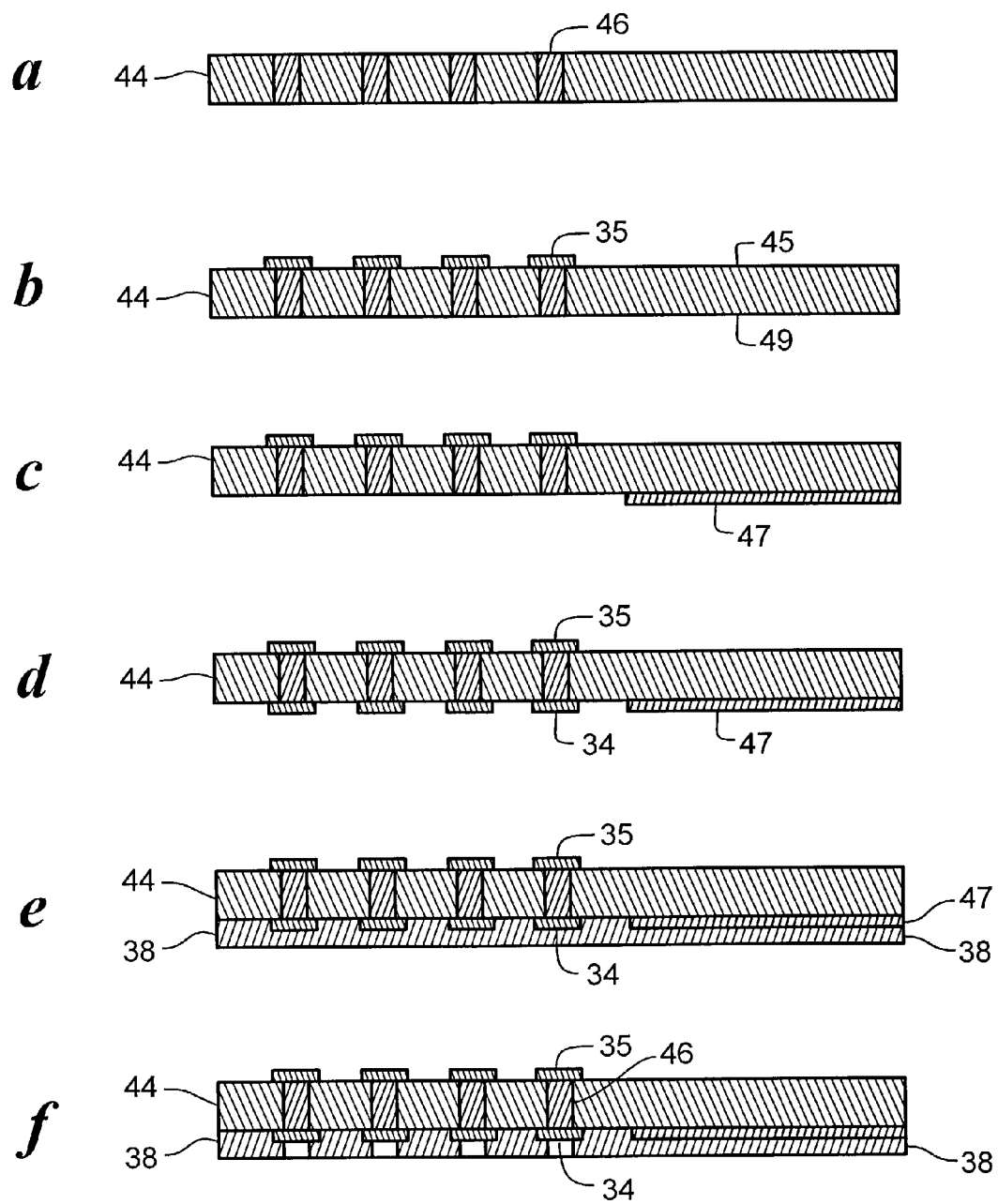
FIG. 10 is a sequence of steps illustrating formation of an integrated interconnect by vapor deposition.
Figure 10:
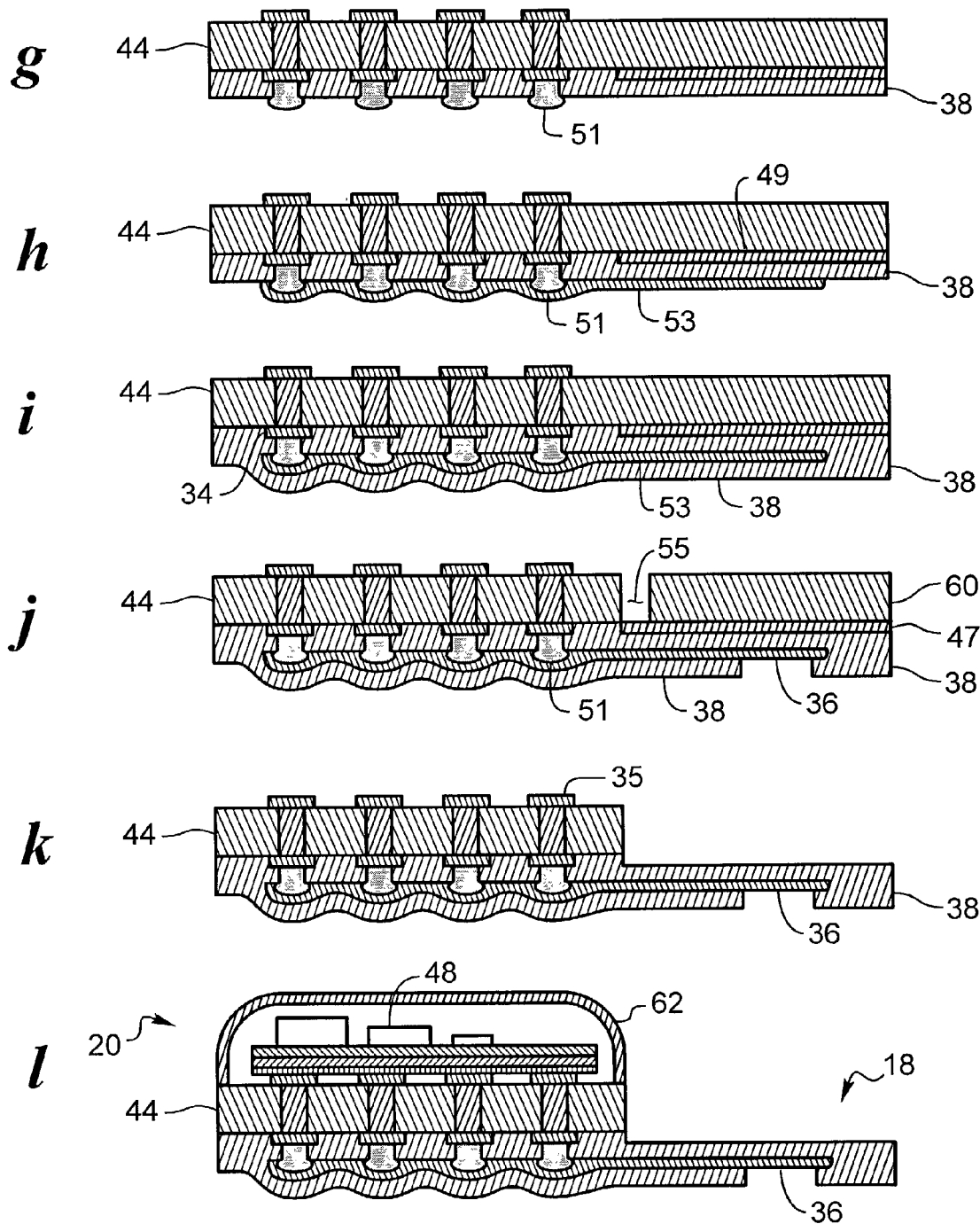

FIG. 10 illustrates a further alternative embodiment to creating a flexible circuit that is electrically and adhesively bonded to a hermetic rigid electronics package. In this approach, the flexible circuit is fabricated directly on the rigid substrate. Step a shows the hybrid substrate 44, which is preferably a ceramic, such as alumina or silicon, having a total thickness of about 0.012inches, with patterned vias 46 therethrough. The vias 46 are preferably comprised of frit containing platinum.

In step b, the routing 35 is patterned on one side of the hybrid substrate 44 by known techniques, such as photolithography or masked deposition. It is equally possible to form routing 35 on both sides of the substrate 44. The hybrid substrate 44 has an inside surface 45 and an outside surface 49. The routing 35 will carry electrical signals from the integrated circuit, that is to be added, to the vias 46, and ultimately will stimulate the retina (not illustrated). The routing 35 is patterned by know processes, such as by masking during deposition or by post-deposition photolithography. The routing 35 is comprised of a biocompatible, electrically conductive, patternable material, such at platinum.

Step c illustrates formation of the release coat 47 on the outside surface 49 of the hybrid substrate 44. The release coat 47 is deposited by known techniques, such as physical vapor deposition. The release coat 47 is removable by know processes such as etching. It is preferably comprised of an etchable material, such as aluminum.

Step d illustrates the formation of the traces 34 on the outside surface 49 of the hybrid substrate 44. The traces 34 are deposited by a known process, such as physical vapor deposition or ion-beam assisted deposition. They may be patterned by a known process, such as by masking during deposition or by post-deposition photolithography. The traces 34 are comprised of an electrically conductive, biocompatible material, such as platinum or platinum alloys, such as platinum-iridium, or titanium-platinum. The traces 34 conduct electrical signals along the flexible circuit 18 and to the stimulating electrode array 10, which were previously discussed and are illustrated in FIG. 4.

Step e illustrates formation of the flexible electrically insulating substrate 38 by known techniques, preferably liquid precursor spinning. The flexible electrically insulating substrate 38 is preferably comprised of polyimide. The flexible electrically insulating substrate electrically insulates the traces 34. It is also biocompatible when implanted in living tissue. The coating is about 5 microns thick. The liquid precursor is spun coated over the traces 34 and the entire outside surface 49 of the hybrid substrate 44, thereby forming the flexible electrically insulating substrate 38. The spun coating is cured by known techniques.

Step f illustrates the formation of voids in the flexible electrically insulating substrate 38 thereby revealing the traces 34. The flexible electrically insulating substrate is preferably patterned by known techniques, such as photolithography with etching.

Step g illustrates the rivets 51 having been formed over and in intimate contact with traces 34. The rivets 51 are formed by known processes, and are preferably formed by electrochemical deposition of a biocompatible, electrically conductive material, such as platinum or platinum alloys, such as platinum-iridium.

Step h illustrates formation of the metal layer 53 over the rivets 51 in a controlled pattern, preferably by photolithographic methods, on the outside surface 49. The rivets 51 and the metal layer 53 are in intimate electrical contact. The metal layer 53 may be deposited by known techniques, such as physical vapor deposition, over the entire surface followed by photolithographic patterning, or it may be deposited by masked deposition. The metal layer 53 is formed of an electrically conductive, biocompatible material, which in a preferred embodiment is platinum. The patterned metal layer 53 forms traces 34 and electrodes 36, which conduct electrical signals from the electronics control unit 20 and the electrodes 36 (see FIGS. 4 and 5).

Step i illustrates the flexible electrically insulating substrate 38 applied over, the outside surface 49 of the rigid substrate 44, as in step e. The flexible electrically insulating substrate 38 covers the rivets 51 and the metal layer 53.

Step j illustrates the hybrid substrate 44 having been cut by known means, preferably by a laser or, in an alternative embodiment, by a diamond wheel, thereby creating cut 55. The portion of hybrid substrate 44 that will be removed is called the carrier 60.

The flexible electrically insulating substrate 38 is patterned by known methods, such as photolithographic patterning, or it may be deposited by masked deposition, to yield voids that define the electrodes 36. The electrodes 36 transmit electrical signals directly to the retina of the implanted eye (see FIG. 4)

Step k illustrates flexible circuit 18 attached to the hybrid substrate 44. The carrier 60 is removed by utilizing release coat 47. In a preferred embodiment, release coat 47 is etched by known means to release carrier 60, leaving behind flexible circuit 18.

Step I illustrates the implantable electronic device of a flexible circuit 18 and an intimately bonded hermetic electronics control unit 20. The electronics control unit 20, which contains the microelectronics assembly 48, is hermetically sealed with header 62 bonded to rigid circuit substrate 44. The header 62 is comprised of a material that is biocompatible when implanted in living tissue and that is capable of being hermetically sealed to protect the integrated circuit electronics from the environment.

Figure 11:
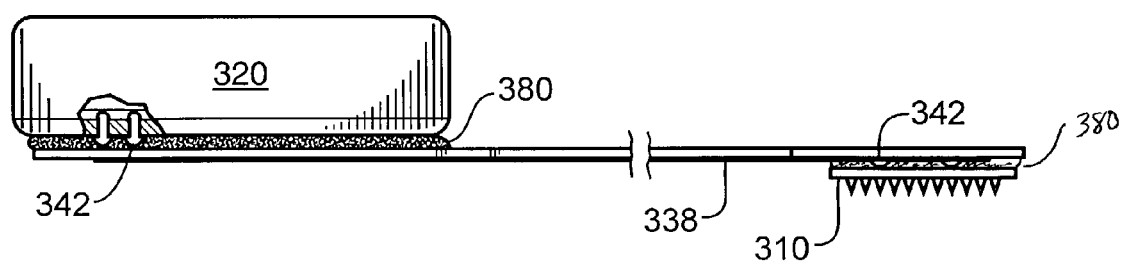
FIG. 11 is a side view of a flexible circuit bonded to a rigid array.

FIG. 11 illustrates an electronics control unit 320 attached to flexible electrically insulating substrate 338, which is preferably comprised of polyimide, by bonded connections 342. The electronics control unit 320 is preferably a hermetically sealed integrated circuit, although in an alternative embodiment it may be a hermetically sealed hybrid assembly. Bonded connections 342 are preferably conductive adhesive, although they may alternatively be solder bumps. The bond area is underfilled with an adhesive 380. Rigid stimulating electrode array 310 is attached to the flexible electrically insulating substrate 338 by bonded connections 342.

Figure 12:
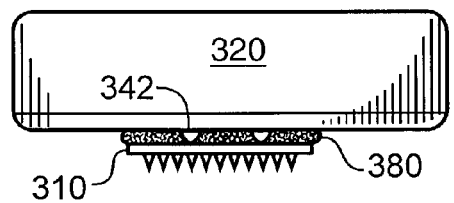
FIG. 12 is a side view of an electronics control unit bonded to a rigid array.

FIG. 12 illustrates an electronics control unit 320 attached to rigid stimulating electrode array 310 by bonded connections 342. The bond area is then underfilled with an adhesive 380, preferably epoxy. Bonded connections 342 are preferably conductive adhesive, although they may alternatively be solder bumps.

Accordingly, what has been shown is an improved flexible circuit with an electronics control unit attached thereto, which is suitable for implantation in living tissue and to transmit electrical impulses to the living tissue. Obviously, many modifications and variations of the present invention are possible in light of the above teachings. It is therefore to be understood that, within the scope of the appended claims, the invention may be practiced other than as specifically described.

What is claimed is:

1. An implantable device comprising:
   a substrate containing electrically conductive feedthroughs forming electrically conductive pads on a first side of said substrate;
   a first flexible electrically insulating layer on said first side of said substrate;
   said first flexible electrically insulating layer defining voids adjacent to said conductive pads;
   a flexible electrically conducting layer on. said first flexible electrically insulating layer wherein at least a portion of said flexible electrically conducting layer physically contacts said conductive pads; and
   a second flexible electrically insulating layer on said flexible electrically conducting layer.

2. The implantable device according to claim 1, wherein said substrate is a rigid substrate.

3. The implantable device according to claim 1, wherein a portion of said substrate is removed.

4. The implantable device according to claim 1, wherein at least one of said first electrically insulating layer or said second flexible electrically insulating layer defines additional voids remote to said substrate.

5. The implantable device according to claim 1, further comprising an electrical circuit on said substrate.

6. The implantable device according to claim 5, further comprising a hermetic package enclosing said electrical circuit.

7. The iinplantable device according to claim 1, wherein the substrate comprises an integrated circuit.

8. The implantable device according to claim 7, where said itnegrated circuit is within a hermetic package.

9. The implantable device according to claim 7, where said substrate a hybrid circuit.

10. The impiantable device according to claim 1, wherein any of said voids are formed by laser cutting.

11. The implantable device according to claim 1, wherein any of said voids are formed by plasma etching.

12. The implantable device according to claim 1, wherein any of said layers are formed by ion-beam assisted deposition.

13. The implantable device according to claim 1, wherein said implantable device is a neural interface.

14. A method of making an implantable device comprising:
prov014ing a substrate containing electrically conductive feedthroughs forming electrically conductive pads on a first side of said substrate;
depositing a first flexible electrically insulating Layer on said first side of said substrate;
defining voids in said first flexible electrically insulating layer adjacent to said conductive pads;
depositing a flexible electrically conducting layer on said first flexible electrically insulating layer where at least a portion of said flexible electrically conducting layer and physically contacts said conductive pads; and
depositing a second flexible electrically insulating layer on said flexible electrically conductive layer.

15. The method according to claim 14, further comprising the step of releasing at least a portion of said first flexible insulating layer from said substrate.

16. The method according to claim 14, where in said biocompatible metal is comprised of platinum flake.

17. The method according to claim 14, wherein said substrate is a rigid substrate.

18. The method according to claim 14, further comprising the step of cutting away a portion of said substrate.

19. The method according to claim 14, further comprising the step of creating additional voids remote to said substrate in a layer selected from the group consisting of said first electrically insulating layer and said second flexible electrically insulating layer.

20. The method according to claim 14, further comprising the step of forming an electrical circuit on said substrate.

21. The method according to claim 14, further comprising the step of forming a hermetic package enclosing said electrical circuit.

22. The method according to claim 14, wherein the substrate comprises an integrated circuit.

23. The method according to claim 14, wherein any of said voids steps are accomplished by laser cutting.

24. The method according to claim 14, wherein said step of creating voids in said first flexible electrically insulating layer is accomplished by plasma etching.

25. The method according to claim 14, wherein any of said depositing steps are accomplished by ion-beam assisted deposition.

26. An implantable electronic device comprising:
a hermetic electronics control unit,
a first thin film flexible electrically insulating substrate;
an electrically conducting metal layer deposited on said first insulating layer;
a second thin film flexible electrically insulating substrate deposited on said electrically conducting metal layer;
at least one of said first flexible electrically insulating substrate or said second flexible electrically insulating substrate defining holes that expose said electrically conducting metal layer forming contacts and means for bonding said electronics'control unit to said implantable electronic device.

27. The implantable electronic device according to claim 26, wherein said hermetic electronics control unit is an integrated circuit.

28. The implantable electronic device according to claim 26, wherein said hermetic electronics control unit is a hybrid circuit.

29. The implantable electronic device according to claim 26, wherein said means for bonding said electronics control unit to said implantable electronic device is an electrically conductive adhesive.

30. The implantable electronic device according to claim 29, wherein said electrically conductive adhesive is comprised of platinum metal flake.

31. The implantable electronic device according to claim 29, wherein said electrically conductive adhesive is comprised of epoxy or polyimide containing electrically conductive particulate of a biocompatible metal.

32. The implantable electronic device according to claim 31, wherein said biocoinpatible metal is comprised of platinum, iridium, titanium, platinum alloys, iridium alloys, or titanium alloys.

33. The implantable electronic device according to claim 29, wherein said electrically conductive adhesive is comprised of silicone.

34. The implantable electronic device according to claim 26, wherein said means for bonding said electronics control unit to said implantable electronic device is an electrically conductive studbump.

35. The implantable electronic device according to claim 26, wherein said stud bump is comprised of platinum or a platinum alloy.

36. The implantable electronic device according to claim 26, wherein said means for bonding said electronics control unit to said implantable electronic device is a staple.

37. The implantable electronic device according to claim 36, wherein said staple is comprised of platinum or a platinum alloy.

38. The implantable electronic device according to claim 26, wherein said means for bonding said electronics control unit to said implantable electronic device is a tail-ball.

39. The implantable electronic device according to claim 26, wherein said tail-bail is comprised of platinum or a platinum alloy.

40. A method of bonding an iinplantable electronics control unit to a thin film flexible circuit for implantation as a neural interface, said method comprising the steps of:
applying electrically conductive adhesive to input/output contacts of a hybrid substrate,
applying electrically conductive adhesive to bond pads of a flexible electrically insulating substrate,
placing said input/output contacts in alignment with said bond pads, and
curing said conductive adhesive.

41. A method of bonding two implantable devices comprising the steps of:
studbumping bond pads of a first device with biocompatible materials;
studbumping bond pads of a second device with biocompatible materials;
placing said bond pods in alignment; and bonding said studbumps together by a thermomechanical process.

42. The method according to claim 41, wherein said devices are hermetically sealed electronics packages further comprising at least one electrode.

43. The method according to claim 41, wherein said bond pads are further comprised of platinum.

44. The method according to claim 41, wherein said biocompatible materials are comprised of platinum.

45. A method of bonding two implantable devices comprising the steps of:
   studbumping bond pads on a first device with gold studbumps;
   studbumping bond pads on a second device with gold studbumps;
   placing said bond pads in alignment;
   bonding said studbumps together by a thermomechanical process; and
   underfilling space between said first device and said second device with a water resistant insulating material.

46. The method according to claim 45, further comprising the step of plating a least one of said bond pads prior to studbumping.

47. A method of bonding two implantable devices, said method comprising the steps of:
   locating a bond pad of a first substrate;
   modifying said bond pad forming a through hole at the center of said bond pad;
   aligning said through bole of flexible electrically insulating substrate with an input/output contact of a second substrate;
   placing wire across said through bole in said bond pad of said first substrate;
   bonding said wire to said input/output contact and to said bond pad; and
   cutting said wire near said bond pad.

48. The method according to claim 47, wherein said at least one of said devices are hermetically sealed electronics packages further comprising at least one electrode.

49. The method according to claim 47, wherein said bond pads are further comprised of platinum.

50. The method according to claim 47, wherein said biocompatible materials are comprised of platinum.

51. A method of bonding two implantable devices, said method comprising the steps of:
   forming a tail-ball with a tail on a wire;
   bonding said tail-ball to an input/output contact of a first substrate;
   modifying a flexible electrically insulating substrate by forming a through hole adjacent to a bond pad of said second substrate;
   aligning said through hole of said second substrate with said tail;
   placing said tail through said through hole;
   bending said tail to contact said bond pad; and
   bonding said tail to said bond pad.

52. The method according to claim 51, wherein said devices are hermetically sealed electronics packages further comprising at least one electrode.

53. The method according to claim 51, wherein said bond pads are further comprised of platinum.

54. The method according to claim 51, wherein said biocompatible materials are comprised of platinum.

55. The method according to claim 51, further comprising the step of welding a locking wire over said tail and said bond pad.

* * * * *

UNITED STATES PATENT AND TRADEMARK OFFICE
CERTIFICATE OF CORRECTION

| | |
|---|---|
| PATENT NO. | : 7,211,103 B2 |
| APPLICATION NO. | : 10/174349 |
| DATED | : May 1, 2007 |
| INVENTOR(S) | : Robert J. Greenberg et al. |

It is certified that error appears in the above-identified patent and that said Letters Patent is hereby corrected as shown below:

Col. 10 Claim 1 - delete "." in line 48 after the word "on".

Col. 11 Claim 7 - delete "The iinplantable" and insert -- The implantable --.

Col. 11 Claim 8 - delete "where said itnegrated" and insert -- where said integrated --.

Col. 11 Claim 10 - delete "The impiantable" and insert -- The implantable --.

Col. 11 Claim 14 - delete "electrically insulating Layer" and insert -- electrically insulating layer --.

Col. 11 Claim 26 - delete "electrically conducting metal layer forming contacts and means for bonding said electronics' control unit to said implantable electronic device." And insert -- electrically conducting metal layer forming contacts; and means for bonding said electronics control unit to said implantable electronic device. --

Col. 12 Claim 32 - delete "wherein said biocoinpatible" and insert -- wherein said biocompatible --.

Col. 12 Claim 39 - delete "wherein said tail-bail" and insert -- wherein said tail-ball --.

Col. 12 Claim 40 - delete "A method of bonding an iinplantable" and insert -- A method of bonding an implantable --.

Col. 12 Claim 41 - delete "placing said bond pods" and insert -- placing said bond pads --.

UNITED STATES PATENT AND TRADEMARK OFFICE
CERTIFICATE OF CORRECTION

PATENT NO.       : 7,211,103 B2
APPLICATION NO.  : 10/174349
DATED            : May 1, 2007
INVENTOR(S)      : Robert J. Greenberg et al.

It is certified that error appears in the above-identified patent and that said Letters Patent is hereby corrected as shown below:

Col. 13 Claim 47 - delete "aligning said through bole" and insert -- aligning said through hole --; delete "placing wire across said through bole" and insert -- placing wire across said through hole --.

Signed and Sealed this

Third Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,211,103 B2 Page 1 of 1
APPLICATION NO. : 10/174349
DATED : May 1, 2007
INVENTOR(S) : Robert J. Greenberg et al.

It is certified that error appears in the above-identified patent and that said Letters Patent is hereby corrected as shown below:

Title page, item (75) Inventors - insert --Gaillard R. Nolan, Valencia, CA (US); Dao Mln Zhou, Saugus, CA (US)--

Signed and Sealed this

Twenty-second Day of June, 2010

David J. Kappos
*Director of the United States Patent and Trademark Office*